United States Patent [19]

Sawyer

[11] Patent Number: 5,587,360
[45] Date of Patent: Dec. 24, 1996

[54] PLATELET ADHESION INHIBITOR

[75] Inventor: Roy T. Sawyer, Dyfed, United Kingdom

[73] Assignee: Merck Patent GmbH, Darmstadt, Germany

[21] Appl. No.: 39,276

[22] PCT Filed: Oct. 10, 1991

[86] PCT No.: PCT/GB91/01763

§ 371 Date: Apr. 9, 1993

§ 102(e) Date: Apr. 9, 1993

[87] PCT Pub. No.: WO92/07005

PCT Pub. Date: Apr. 30, 1992

[30] Foreign Application Priority Data

Oct. 10, 1990 [GB] United Kingdom ............... 9022040

[51] Int. Cl.$^6$ ..................................................... A61K 38/58
[52] U.S. Cl. ........................... 514/21; 514/12; 530/350; 530/416; 530/858
[58] Field of Search ................ 514/12, 21; 530/350, 530/416, 858

[56] References Cited

U.S. PATENT DOCUMENTS

| | | | |
|---|---|---|---|
| 4,390,630 | 6/1983 | Sawyer et al. | 435/226 |
| 4,588,587 | 5/1986 | Gasic | 424/95 |
| 4,832,849 | 5/1989 | Cardin | 210/635 |
| 5,114,922 | 5/1992 | Maschler et al. | 514/12 |
| 5,139,944 | 8/1992 | Sawyer et al. | 435/226 |
| 5,182,113 | 1/1993 | Rigbi et al. | 424/537 |
| 5,246,715 | 9/1993 | Orevi et al. | 424/550 |

OTHER PUBLICATIONS

Munro et al., Blood Coagulation and Fibrinolysis, vol. 2, pp. 179–184, 1991.
Munro et al., Thrombosis & Haemostasis, vol. 3, pp. 366–369, 1989.
Bagdy et al., "Methods in Enzymology", vol. 45, pp. 669–678, 1976.
Biological Abstracts, vol. 79, No. 11, 1985 (Philadelphia, PA, US) I. P. Baskova et al.: "Secretion of the salivary glands of Hirudo medicinalis inhibits the ADP–induced aggregation of human platelets and platelet adhesion to a collagen–coated surface", abstract 92228, & Byull. Eksp. Biol. Med. 97 (6): 696–699, 1984.
Chemical Abstracts, vol. 107, No. 23, 7 Dec. 1987 (Columbus, Ohio, US) I. P. Baskova et al.: "Mechanisms of inhibition of vascular–platelet hemostasis by salivary gland secretion of the medicinal leech Hirudo medicinalis", abstract 211673n, & Biokhimiya (Moscow) 1987, 52(9), 1461–1468.

Primary Examiner—Chhaya D. Sayala
Attorney, Agent, or Firm—Darby & Darby, P.C.

[57] ABSTRACT

The inhibitor is protein derived leech tissue or leech secretions (for example, from Hirudo medicinalis), which is capable of binding to native collagen, in such a way that substantially no cleavage breakdown products of collagen molecules occur on SDS-PAGE. The protein substantially inhibits collagen-induced platelet aggregation or adhesion, has a molecular weight of 60–70 kilodaltons in reduced form and has optimum activity at pH 8.0.

13 Claims, 5 Drawing Sheets

PLATELET ADHESION INHIBITOR

The present invention is concerned with leech-derived proteins or polypeptides capable of binding to biological substrates such as collagen, as well as other substrates (typically strongly charged substrates, such as ionically negatively charged substrates) and inhibiting the adhesion of platelets.

Therapeutic intervention at the level of platelet adhesion/ aggregation is useful for the prevention and treatment of most thrombotic diseases. There are many drugs with inhibitory effects on platelet function, such as aspirin, which interferes with the arachidonic pathway by inhibition of the enzyme cyclooxygenase. In the latter pathway, the arachidonic acid (produced by the collagen induced stimulation of phospholipase $A_2$ within the platelets) is converted through the action of cyclooxygenase to thromboxane $A_2$.

Leech saliva contains several known agents capable of inhibiting platelet aggregation, notable amongst these being:
1. Hirudin a naturally occurring polypeptide which is produced by the leech *Hirudo medicinalis*. Hirudin prevents thrombin-induced platelet aggregation by binding tightly to thrombin in a 1:1 stoichiometric complex. This in turn inhibits thrombin-catalysed conversion of fibrinogen to fibrin.
2. A low molecular weight receptor-mediated platelet activating factor antagonist derived from saliva of Hirudinidae having inhibitory activity against platelet aggregation induced by aggregating agents such as PAF-acether is disclosed in EP-A-0348208A.
3. A collagenase which specifically degrades collagen by means of hydrolyric scission of peptide bonds in helical regions of the collagen molecule is disclosed in WO87/ 00860.
4. An apyrase which prevents ATP/ADP mediated events, is described by Rigbi et al
   in Comp. Blochem. Physiol. 87B, pp.567–574, 1987.

However, a substance which can bind to the surface of a biological substrate such as collagen and which has a non-endopeptidase interaction with the biological substrate, such that collagen induced platelet aggregation is inhibited, has not previously been disclosed.

The present invention is concerned with a protein, derived from leech tissue or leech secretions, having a non-endopeptidase binding mechanism with collagen.

According to the present invention, therefore, there is provided a protein or polypeptide derived from leech tissue or leech secretions, which is capable of binding directly or indirecfly to collagen, the nature of the protein-collagen binding interaction being such that substantial cleavage of the pepfide bonds present in the collagen molecules does not occur on SDS-PAGE. The binding may be direct to collagen or to an intermediary such as a ligand or Von Willebrand's factor, which intermediary is itself bound to a collagen.

When referring to the protein being "derived" from leech tissue or leech secretions, we intend to encompass not only the isolation of the protein from leech tissue or leech secretions, but also the production of synthetic equivalents by techniques such as recombinant DNA synthesis which involve isolation of the protein and then using the isolated material as the starting material for quantity production of the equivalent protein (and also shortened polypeptide analogues with comparable binding properties).

The present invention therefore further comprises a recombinant or protein engineered equivalent to the leech derived protein according to the invention.

The protein according to the invention has a molecular weight of approximately 65 kilodaltons in reduced form (that is about 60–70 kilodaltons) and is derived from the saliva or tissue of blood-sucking leeches, including, but not restricted to, *Hirudo medicinalis*.

The protein according to the invention binds to exposed collagen so as to prevent the normal process of platelet adhesion/aggregation at sites of tissue injury and/or disease. This phenomenon is exemplified by the observations that the protein according to the invention has a rapid effect on collagen. The rapid non-enzymic effects of the protein on collagen are reflected in its ability to suppress collagen-induced platelet aggregation, adhesion of platelets to collagen-coated microcarrier beads and in its ability to cause flocculation of collagen fibril suspensions.

The leech-derived protein according to the invention has a pH optimum for activity at substantially pH 8.0. Activity falls off at a pH lower than the physiological pH (7.4), less than 20% of the original activity being detected at pH 6.5. The protein is further characterised in that the co-factors Ca++ and to a lesser extent Mg++ are required for optimum activity.

The protein is not a collagenase and is therefore fundamentally different from the known leech-derived collagenase. SDS-PAGE analysis of the products of incubations of the protein with type I collagen at 37 degrees Celsius showed no detectable changes in the collagen SDS-PAGE pattern, indicating that the protein is not a collagenase. Surprisingly, the protein can actually prevent autolytic denaturation of solubilised Type I collagen which can occur over prolonged incubation.

In addition to the above difference, the protein is isolated using entirely different procedures from those for the isolation of leech collagenase. To reinforce this point, we have found that the purification procedure (gel filtration) previously used to isolate leech collagenase does not result in isolation of the protein according to the invention. Using standard techniques the protein absorbs strongly to chromatography matrices and hence special techniques, described herein, are necessary to prevent adsorption and to isolate the protein.

These and other differences, exemplified below, differentiate the protein from leech-derived collagenase and this is in itself surprising and new.

Hence there is further provided a method of preparation of a leech derived protein having a non-lyric binding mechanism with collagen, which comprises isolation of leech secretion or extraction of leech tissue, anion exchange chromatography of the resulting tissue extract or secretion so as to substantially remove himdin anti-thrombin activity, and further purification of the purified material by cation exchange chromatography.

The method preferably involves the use of ethanol-containing buffers throughout so as to substantially prevent loss of the protein by adsorption to surfaces of apparatus, the ethanol being subsequently removed from the isolated protein. A preferred such buffer is 20 mM Tris HCl, 10 mM $CaCl_2$, 12% ethanol, pH 7.5.

The invention also comprises pharmaceutical or veterinary formulations which comprise as active components therapeutically effective amounts of the leech-derived protein according to the invention (either alone or together with other active ingredients, examples of which include anticoagulants, such as himdin or heparin, and thrombolytic agents such as a plasminogen activator or hementin), and a pharmaceutically acceptable carrier.

The pharmaceutical or veterinary formulations of the present invention may be used for treatment of several pathological conditions involving platelet aggregation and also for preventing platelet aggregation. Thus, the pharmaceutical or veterinary formulations according to the present invention may be used for the treatment of various thromoembolic disorders, including venous thrombosis, peripheral arterial thrombosis, cerebrovascular thrombosis and myocardial infarction, as well as for patients with arteriovenous shunts, or undergoing coronary bypass surgery. The formulations may also be used for preventing the rejection of allografts (such as kidney, liver or heart), and for the treatment of autoimmune disease, including lupus erythematosus, rheumatoid arthritis and polyarthritis nodosa.

A further embodiment of the invention comprises the use of leech-derived protein having a non-endopeptidase binding mechanism with collagen, in which the protein is immobilised on a surgical device so as to render the surface biocompatible and thromboresistant. Such devices sometimes have wettable surfaces which typically induce platelet aggregation, which is a disadvantage in their intended uses in implantable and extracorporeal devices in contact with body fluids; examples thereof include prostheses and sutures.

The preservation of artificial organs, cardiac valves and other prosthetic devices, artificial vascular segments, catheters and other robing carrying blood, by treatment of such devices with the leech-derived protein is also contemplated according to the present invention.

The formulations according to the invention are also useful in simulating the prolonged bleeding phenomenon experienced after leech bites and may therefore substitute, entirely or in part, for the leech in those applications in plastic surgery and microsurgery which are currently indicated for the leech.

There is also provided, therefore, a leech-derived protein having a non-endopeptidase binding mechanism for collagen, which can be incorporated as an active component in a pharmaceutical or veterinary formulation, for use in maintaining prolonged bleeding following plastic surgery or microsurgery; the protein being used alone or in conjunction with one or more leeches.

The formulations according to the invention may be administered as unit doses containing conventional non-toxic pharmaceutically acceptable carriers, diluents, adjuvants and vehicles as appropriate, typically for parenteral administration. The term "parenteral" as used herein includes subcutaneous, intravenous, intra-articular and intratechal injection and infusion techniques. Unit doses according to the invention may contain daily required amounts of the protein according to the invention, or submultiples thereof to make up the desired dose. The optimum therapeutically acceptable dose for a given patient depends upon a variety of factors, such as the activity of the specific active material employed, the age, body weight, general health, sex, diet, time and route of administration, rate of clearance etc.

As used herein, the term "pharmaceutically acceptable carrier" means an inert, non-toxic solid or liquid filler, diluent or encapsulating material, not reacting adversely either with the active ingredient or with the patient. Suitable carriers are known to those versed in the art. Wetting agents, emulsifiers, slow release agents, coating agents and preservatives can also be present in the formulations according to the invention. The amount of active ingredient used with the carrier to produce a single dosage form will vary depending upon the patient treated and the particular mode of administration.

The cartier may be a pharmaceutically acceptable gel base or cream, suitable for coating, prior to use, in-dwelling catheters, vascular shafts or artificial organs, which devices. are usually made from plastics materials and synthetic fibres. Coating such devices with formulations according to the invention may be useful in preventing platelet adherence thereto after insertion.

The present invention further provides a method of inhibiting platelet aggregation, and treating and preventing the above-mentioned pathological conditions and thromboembolic disorders, which comprises administering to a patient a pharmaceutical or veterinary formulation according to the invention.

The compositions of matter, pharmaceutical or veterinary formulations and methods of the present invention will be illustrated by reference to the following examples.

EXAMPLE 1. ISOLATION OF THE PROTEIN

Figure 1:
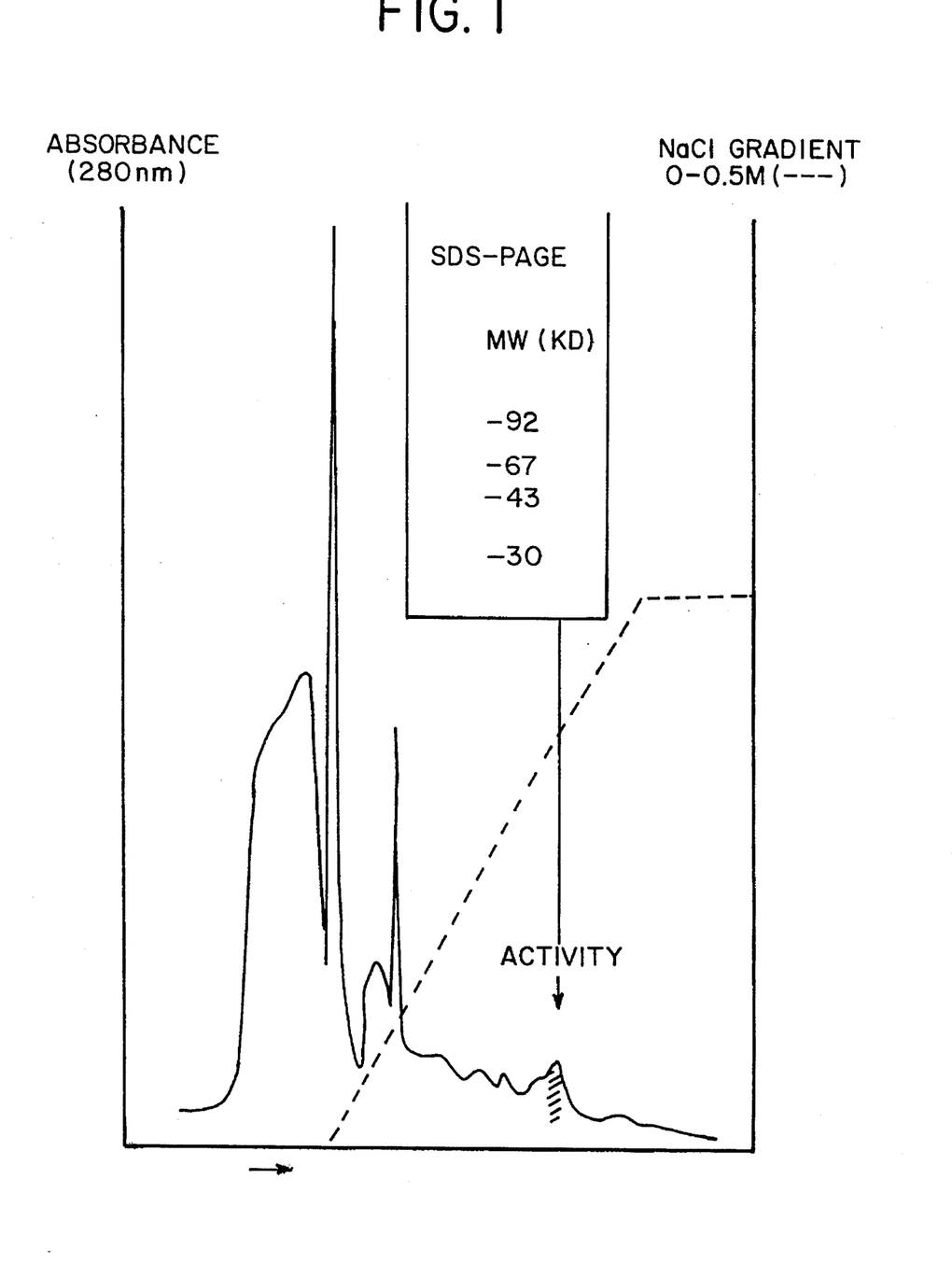
FIG. 1 is a typical example of a high performance cation exchange chromatography, using a NaCl gradient.

The protein according to the invention could not be isolated from crude leech saliva unless special precautions were taken to prevent adsorption of the activity to column matrices (see below Examples 4,5). For this reason, at least one blocking agent (such as ethanol) is included in the purification buffers and is subsequently removed by freeze drying for all studies involving platelets. The purification buffer used is 20 mM Tris HCl, 10 mM $CaCl_2$, 12% ethanol, pH 7.5. Fractionation of "leech saliva" by artion exchange column chromatography resulted in a three fold enrichment of protein activity with removal of hirudin anti-thrombin activity which remained absorbed to the gel. Post-anion exchange material was concentrated (5–10 fold) by ultrafiltration and then further purified (>300 fold) by high performance cation exchange chromatography. eluted using an NaCl gradient—a typical example of which is shown in FIG. 1.

The product was analysed by SDS-PAGE on 12.5% polyacrylamide minigels. Samples were reduced with mercaptoethanol. Protein bands on gels were visualised by silver staining.

EXAMPLE 2. ACTIVITY OF THE PROTEIN AGAINST CHROMOGENIC SUBSTRATES

We could not detect significant activity against the chromogenic substrates FALGPA or 4-phenylazobenzyl oxycarbonyl-L-prolyl-L-leucyl-glycyl-L-prolyl-D-arginine which are commonly used to measure collagenase activity. Any hydrolysis of the chromogenic substrates. S2251, S2586, S2288. SAPP or SAAAP that occured over prolonged incubation (12–24 h) at 37 degrees Celsius was of a non-specific nature. However, the protein did have activity against AZO-COLL. a non-specific chromogenic substrate for several proteolytic enzymes. A preferred assay method is described below. Preparations for assay are reconstituted or diluted in assay buffer: 50 mM Tris, 0.2M NaCl, 0.05% casein (Hammerstan grade from British Drug Houses), 0.1% Brij 35, 0.01% sodium azide, pH8.0. Activity is det.ermined using modification of the AZOCCLL assay adapted to microtitre plates. Aliquots (100 microliters) of protein. in a range of dilutions in assay buffer, are incubated with a suspension of washed substrate (100 microliters: 10mg/ml) at 37 degrees Celsius. At the end of the incubation period which varies according to the experiment and dose of protein, the undigested substrate is sedimented by centrifugation and aliquots (100 microliters) of the supernatants transferred to another plate in which the absorbance at 560 nm is measured. Protein activity can be expressed as milliequivalent units of bacterial collagenase (*Clostridium histolyticum*) assayed at the same time under the same conditions.

EXAMPLE 3. CHARACTERISATION OF THE PROTEIN

The protein (5000 units/ml of a preparation of specific activity of 10,000–20,000 units/mg protein) was incubated for 12 hours at 37 degrees Celsius with the appropriate substrate. in assay buffer adjusted to a pH range of between 6–8.5. The activity is expressed as the percentage of that obtained at the optimal pH, pH 8.0. The results (Table 1) show that activity falls off quickly at a pH lower than the. physiological pH, 7.4. such that at pH 6.5 there is about 20% of the original activity detected.

TABLE 1

| pH | Activity (% maximal) |
|---|---|
| 6.0 | 9.0 |
| 6.5 | 21.0 |
| 7.0 | 47.0 |
| 7.5 | 72.0 |
| 8.0 | 100.0 |
| 8.5 | 88.0 |

The protein (3000 units/ml of preparations of specific activity 10,000–20–000 units/mg protein) was incubated for 12 hours at 37 degrees Celsius in assay buffer containing $MgCl_2$, $CaCl_2$ or NaCl at the concentrations shown. Activity was determined and expressed as percent of the maximal adsorbance measured. The results (Table 2) show that the activity of the protein required the presence of $Ca^{++}$ ions and $MS^{++}$ ions to a lesser extent. Even relatively high levels of salt (0.5M) appeared to have little effect on activity.

TABLE 2

| Salt | (mM) | Activity (% maximal) |
|---|---|---|
| NaCl | 750 | 111 |
|  | 600 | 110 |
|  | 450 | 109 |
|  | 300 | 108 |
|  | 150 | (100) |
| $CaCl_2$ | 50 | (100) |
|  | 25 | 85 |
|  | 12.5 | 56 |
|  | 6.3 | 49 |
|  | 3.2 | 44 |
| $MgCl_2$ | 50 | (100) |
|  | 25 | 56 |
|  | 12.5 | 40 |
|  | 6.3 | 36 |
|  | 3.2 | 28 |

The thermostability of the activity was studied at various temperatures. The protein (5000 units/ml of a preparation of 10,000–20,000 units/mg. protein) was pre-incubated for up to 24 hours in assay buffer at temperature up to 100 degrees Celsius and then further incubated for 12 hours at 37 degrees Celsius with substrate. Activity was determined and expressed as a percentage of that of controls which had not been pre-incubated. The results (Table 3) show that the material is relatively stable over 24 hours up to 37 degrees Celsius. At higher temperatures it was found that $Ca^{++}$ ions exerted a protective effect such that at 60 degrees Celsius activity was destroyed within 5 minutes in the absence of $Ca^{++}$ but preserved for more than one hour in the presence of $Ca^{++}$.

TABLE 3

|  | Time | | | | | | | | |
|---|---|---|---|---|---|---|---|---|---|
|  | 30 mins | | 60 mins | | 120 mins | | 12 h | | 24 h |
| + Ca | + | − | + | − | + | − | + | | − |
| 25° C. | 102 | 101 | 103 | 103 | 98 | 107 | 97 | 95 | 96 | 98 |
| 37° C. | 103 | 105 | 107 | 98 | 112 | — | 102 | 97 | 104 | 91 |
| 60° C. | 90 | 0 | 60 | 0 | 16 | 0 | 0 | 0 | — | — |
| 100° C. | 0 | 0 | — | — | — | — | — | — | — | — |

The effect of some typical inhibitors was examined. The protein (5000 units/ml of a preparation of specific activity 10,000–20,000 units/mg) was incubated with DTT, cysteine, EDTA and leech anti-chymotrypsin in a range of concentrations with substrate. The results of any effect on activity were expressed as the dose of inhibitor which gave half maximal inhibition. The effects of orthophenanthroline (2 mM): TIMP (tissue inhibitor of metallo-proteinase) 0.4 micrograms with APMA (0.5 mM) and with pre-incubation for 15 min): SBTI (7.5 micrograms and 30 min pre-incubation): and PMSF (2 mH with 30 min pre-incubation) were also studied. The results (Table 4) show that reducing agents (dithiothreitol and cysteine) destroyed activity. as did the Ca chelating agent, EDTA. Ortho-phenanthroline and TIMP did not inhibit activity; neither did PMSF, soybean trypsin inhibitor, sodium azide nor a preparation of leech anti-chymotrypsin/elastase.

TABLE 4

| Inhibitor | IC50 (mM) |
| --- | --- |
| Dithiothreitol | 0.2 |
| Cysteine | 3.0 |
| EDTA | 2.0 |
| Leech anti-chymotrypsin | No effect |
| o-Phenanthroline | No effect |
| TIMP | No effect |
| SBTI | No effect |
| PMSF | No effect |

We could not detect significant levels of neutral proteinase activity in the protein preparations as assessed using a caseinolytic proteinase detect. ion kit or assays measuring the absorbance at 254/280 nm in the supernatant after incubation 24 h at 37 degrees Celsius and precipitation (with TCA) of albumin, transferpin, or casein.

EXAMPLE 4. SURFACE ACTIVE PROPERTIES OF THE PROTEIN

Table 5 shows the binding of activity to a simple gel filtration matrix, Sephadex G25 and recovery of activity by inclusion of casein, detergent or ethanol.

TABLE 5

Adsorption of the protein to Sephadex G25: Effect of various elution buffers.

| Elution Condition | Recovery (%) |
| --- | --- |
| Water | <1.0 |
| A: 50 mM Tris HCl, pH 7.5 | <1.0 |
| A + 0.1% Triton X100 | <1.0 |
| A + 0.1M CaCl$_2$ | <1.0 |
| A + 1M NaCl | <1.0 |
| A + 2% albumin | 20–50 |
| A + 2% albumin + 0.1% Triton X100 | 20–50 |
| A + 0.1% casein | 80–100 |
| A + 1.0% casein + 0.1% Triton X100 | 80–100 |
| A + 0.1% casein × 0.1% Brij 35 | 80–100 |
| A + 12% Ethanol | 70–100 |

The protein adsorbs to a variety of materials. such as glass, and materials from which filters are constructed.

TABLE 6

| Material | Adsorption (%) |
| --- | --- |
| Cellulose nitrate | 100 |
| Cellulose acetate | 100 |

TABLE 6-continued

| Material | Adsorption (%) |
| --- | --- |
| Glass | 100 |
| Glass fibre | 100 |
| Polystyrene | <10 |
| Polypropylene | <10 |
| Siliconised glass | <10 |

A further example of the protein adsorption to gel matrices which is a property that differentiates it from leech collagenase is given in Example 5.

EXAMPLE 5. NON-COLLAGENASE NATURE OF THE PROTEIN

The following experiments further distinguish the properties of the protein according to the invention from the collagenase disclosed in WO87/00860.

SDS-PAGE of Type I collagen treated with the protein

Figure 2:
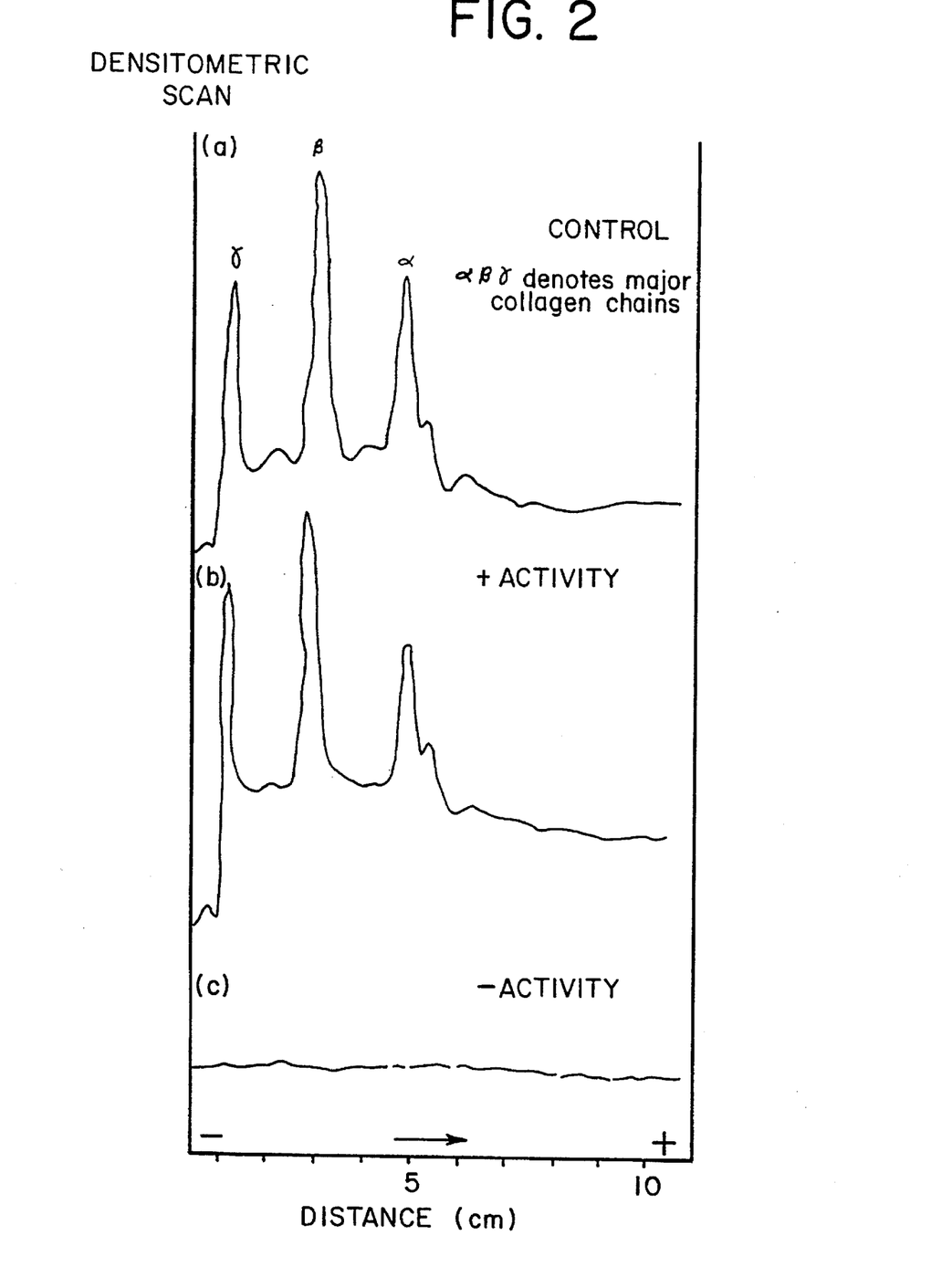
FIG. 2 shows a SDS-PAGE analysis of the product of Type I collagen treated with the protein.

The product of treatment of Type I collagen (calf skin) with the protein was examined by SDS-PAGE analysis (FIG. 2). Type I calf skin collagen (approx 1 mg pieces) (a) was incubated for 24 h at 37 degrees Celsius with the protein according to the invention (b) (1–5000 u/ml) or without (c). Assay buffer was 20 mM Tris. 10 mM CaCl$_2$, 0.2M NaCl, 0.1% Brij 35, pH 8.0. After incubations the reaction tubes (b and c) were centrifuged (10,000 g) to remove any unsolubilised material and the supernatant analysed by SDS-PAGE under reducing conditions (7.5% gel). The results (FIG. 2) showed that following protein treatment (24 h at 37 degrees Celsius), the number and size of the major collagen bands (alpha, beta and gamma) that were revealed were the same as the untreated controls (a). This indicated that no endopeptidase activity had occurred (which would have resulted in lower molecular weight fragments). In other incubations without the protein, extended (1–2 days) incubation over long periods at 37 degrees Celsius frequently resulted in degradiation of solubilised collagen bands to low molecular weight fragments.

The time course of this degradation varied from collagen preparation to preparation. The addition of the protein was able to preserve the uncleaved collagen bands and delay the autolysis of solubilised collagen. The significance of this is not yet understood, but is further evidence of some sort of non-lytic interaction between collagen and the protein.

Gel filtration of the protein

Crude leech saliva containing the protein was prepared, applied to a gel filtration column (Superdex 200) and eluted as described for the purificatior. of leech collagenase (WO87/00860) in 0.2M ammonium bicarbonate pH7.8, Fractions were collected (10 ml) and assayed for activity by incubation with chromogenic substrate for 72 h at 37 degrees Celsius (FIG. 3), Controls were load sample further diluted ×8 to compensate for column dilution.

Figure 3:
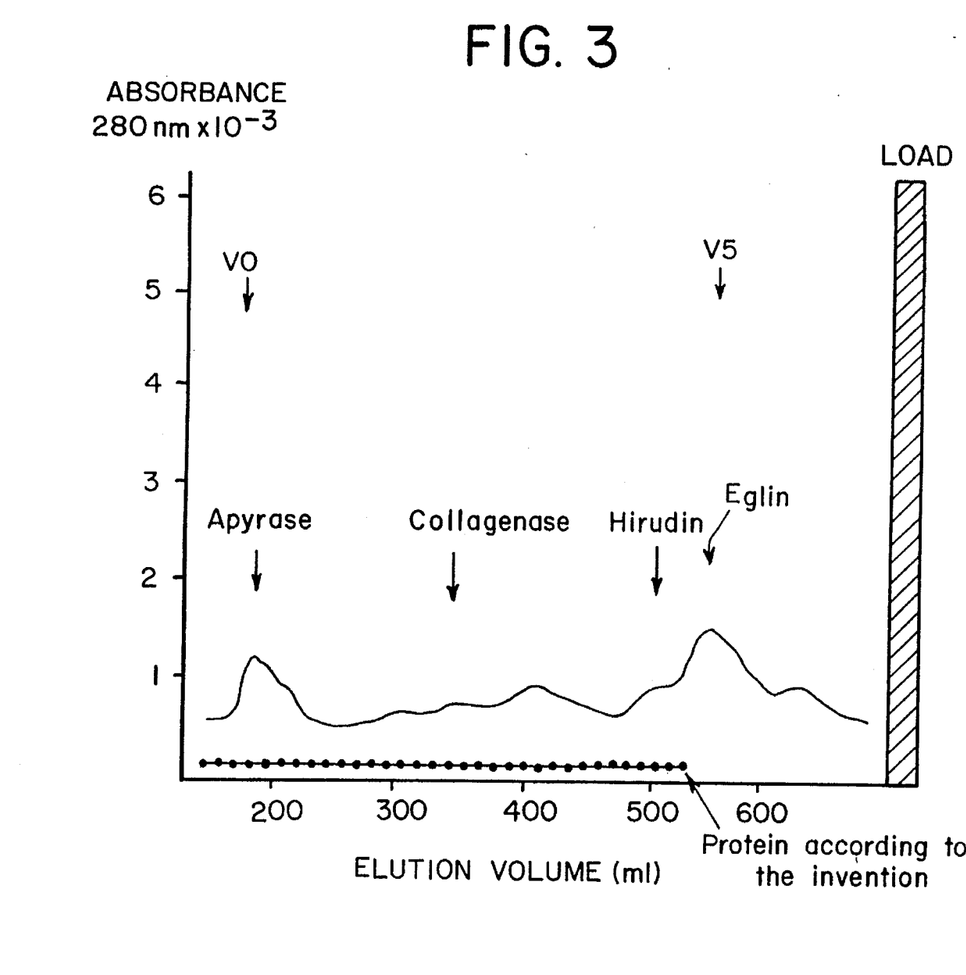
FIG. 3 shows results from assays for activity (by incubation with chromogenic substrate) of crude leech saliva fractions collected from a gel filtration column.

No protein activity was detected in any of the fractions eluted from the column even over prolonged incubation for 3 days at 37 degrees Celsius despite there being maximal activity (at 8 fold dilution in elution buffer) within 5 hours in the control samples. This showed that under the conditions used to isolate leech collagenase, the protein according to the invention could not be isolated because it adsorbed to the column.

EXAMPLE 6. BINDING OF THE PROTEIN TO COLLAGEN FIBRIL SUSPENSIONS

The experiments described below show that the protein can bind rapidly to Type I collagen and this exemplifies the surface active properties of the protein in a biological context. The preparations or controls (100 microliters) were added to a suspension of Type I collagen fibrils (900 microliters) in saline (10 micrograms/ml) and incubated with gentle shaking at room temperature for 1–10 min. The controls were:
a. Boiled protein according to the invention:
b. 20 mM Tris, pH 8.0;
c. 20 mM $CaCl_2$;
d. 20 mM Tris, 20 mM $CaCl_2$, 1.2M NaCl, pH 8.0:
e. 50 mM Tris, 10 mM EDTA, 0.15M NaCl, pH 7.5:
f. 1M Tris, 1M NaCl, pH 8.0

Figure 4:
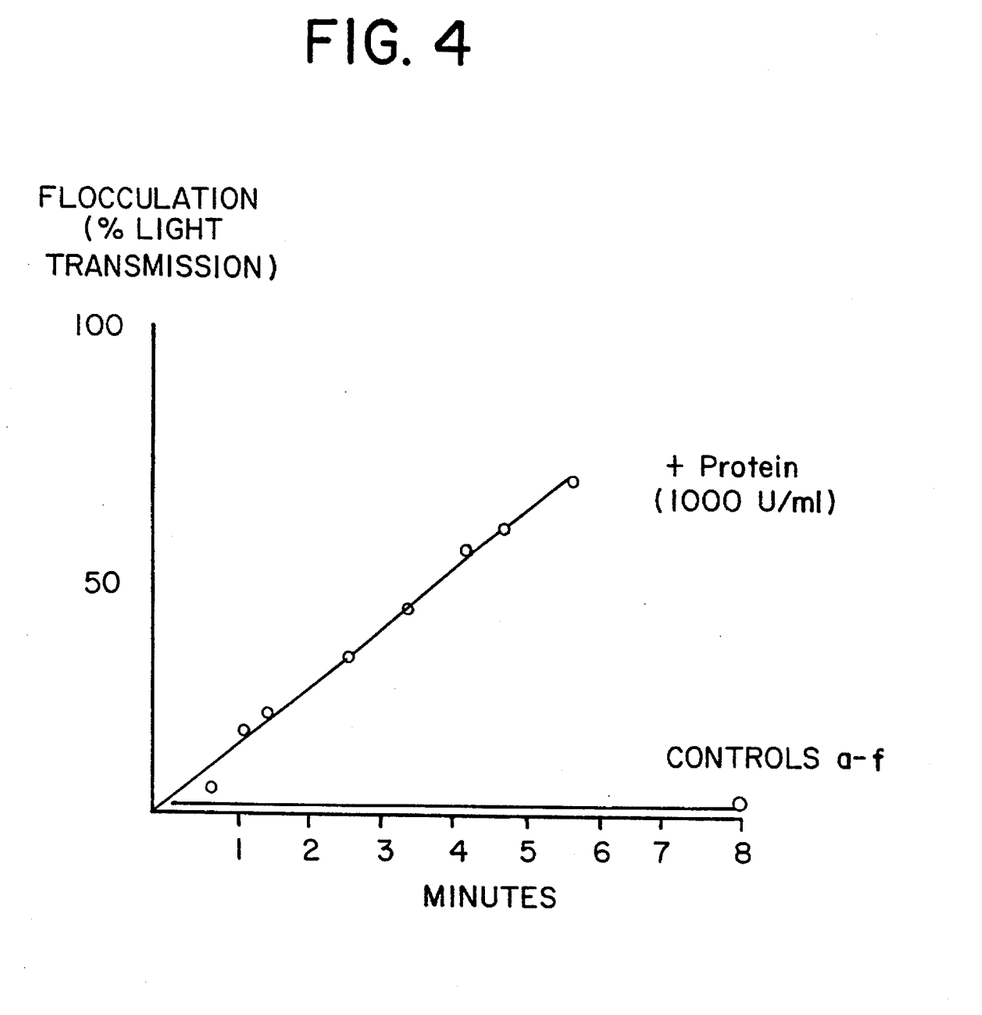
FIG. 4 shows the time dependent flocculation of Type I collagen particles caused by the protein.

The results showed that the protein caused a time dependent flocculation of the collagen particles within the suspension as measured in platelet aggregometer (FIG. 4). A consequence of this flocculation of collagen was complete inhibition of collagen inducible platelet aggregation with these same suspensions (see below). SDS-PAGE analysis of the supernatants following sedimentation of the clumped collagen revealed no significant digestion fragments of collagen generated as a consequence of the flocculation reaction. The experiments were repeated with equivalent or higher concentrations of bacterial collagenase (*Clostridium hystolyticum*) but flocculation of particles was not observed and platelet aggregation was still inducible with the mixture even after 4–5 hours of incubation. A variety of buffer compositions, ionic strengths (up to 2M) and pHs were tried to determine if the effect was an artifact due to buffers or salts, but with no effect apart with phosphate buffered saline where some flocculation was observed upon standing for 24 h at room temperature. Boiling of the protein preparations for 1–2 min destroyed the collagen flocculation ability which is further evidence in favour of it being a property of the protein and not of the vehicle solutions. The incubations after flocculation had occurred were centrifuged and the supernatant and resuspended pellet were assayed for protein activity (Table 7). There was no activity in the supernatant but the resuspended pellets retained activity. This was further evidence for binding of the protein to collagen.

TABLE 7

| Test | Absorbance at 560 nm | |
|---|---|---|
| | Supernatant | Pellet |
| No protein control | 0.15 | — |
| Protein alone | 0.43 | — |
| Collagen + protein | 0.18 | 0.36 |

The protein (5000 units/ml) was incubated at room temperature with type I collagen suspension (10 μg/ml) in 50 mM Tris, 10 mM $CaCl_2$, 0.1% Brij 35, 0.05% casein, 0.01% sodium azide, pH8.0 until flocculation was commmplete (10 min) and then the particles were sedimented and the supernatant and resuspended pellet assayed for activity by incubation for 24 h at 37 degrees Celsius.

EXAMPLE 7. EFFECTS OF PROTEIN ON COLLAGEN-INDUCED PLATELET AGGREGATION

The protein according to the invention was mixed with Type I collagen fibrils (2 min) and acded to platelet rich plasma (0.5 ml) and the course of platelet aggregation followed (final concentrations of protein and collagen were 1000 u/ml and 2 μg/ml respectively). To treated samples, further agonists, bovine thrombin (2 U/ml) or ADP (1μM) was also added after 10 min to confirm platelet reactivity. Aggregation of platelets was measured using an aggregometer.

Figure 5A:
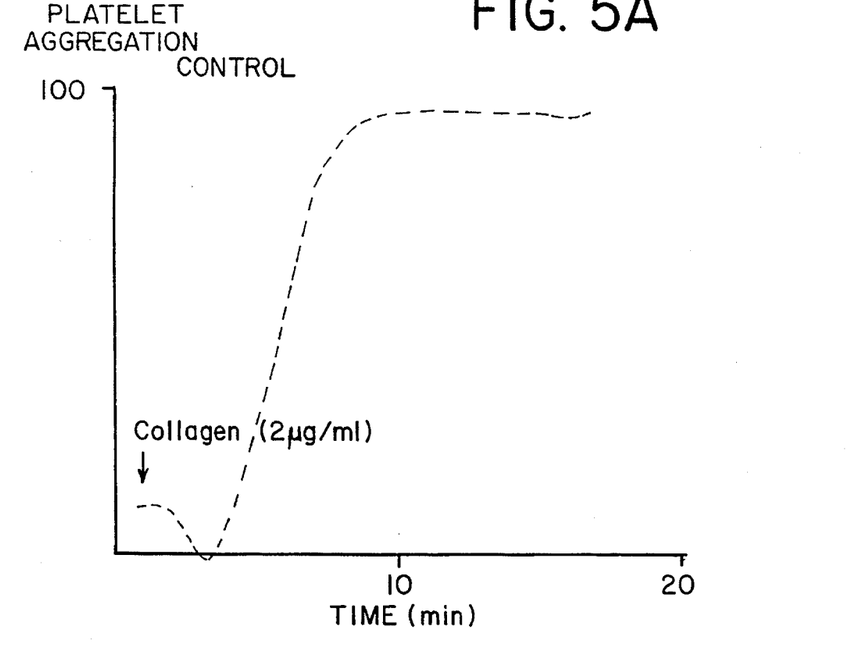
FIG. 5A shows the normal pattern of aggregation in human plasma by collagen.
Figure 5B:
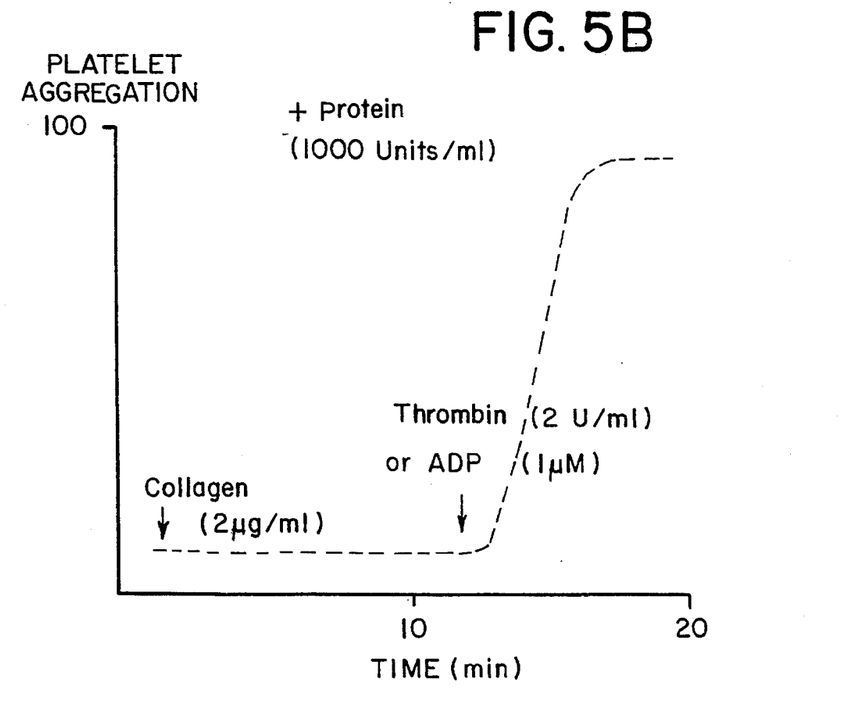
FIG. 5B shows that the doses of the protein (1000–5000 units) have an effect on collagen within 2 mins. such that it is consequently unable to induce platelet aggregation in human plasma.

FIG. 5 shows that doses of the protein (1000–5000 units) have an effect on collagen within 2 min such that it is consequently unable to induce platelet aggr-egation in human plasma. The controls (collagen in vehicle buffer) showed normal patterns of aggregation.

Further addition of ADP (1μM) or thrombin (1–5 U/ml) resulted in normal platelet aggregation, demonstrating that the platelets were still responsive to inducers and that the platelets themselves had not been affected by the protein or the buffer vehicle.

EXAMPLE 8. EFFECT OF THE PROTEIN ON PLATELET ADHESION TO COLLAGEN COATED MICROCARRIER BEADS

Adhesion of platelets to colla, gen was determined by packing a plastic tube with collagen coated microcarrier beads (Sigma) and pumping (Adeplat) human whole blood over them, with or without pretreatment of the beads with the protein followed by counting of the platelet numbers by a Coulter counter.

Precoating of a column of collagen microcarrier beads with two preparations of the protein (5000 units/ml and 1–2000 units/ml desalted) prevented over half the platelets in PRP adhering to the column (Table 8). This phenomenon was observed when the beads had been exposed to the protein for approximately 30 min or less than 2 min, indicating a rapid non-enzymic effect on collagen which prevents platelets adhering.

TABLE 8

| | | Reduction in platelet no. (%) | |
|---|---|---|---|
| Expt No. | Pre-incubation time (minutes) | Control | +Protein |
| 1 | 30 | 60 | 33 |
| 2 | 0–2 | 68 | 36 |
| 3 | 0–2 | 59 | 29 |

Collagen-coated beads were packed into a plastics tube connected to an Adeplat pump apparatus and buffer or protein (Experiment 1,2: 5000 units/ml: Experiment 3: 1–2000 units/ml desalted protein according to the invention) pumped over them immediately followed by fresh whole blood. The number of platelets collected in the flow through was counted in a Coultep counter.

EXAMPLE 9. PREVENTION OF PLATELET ADHESION TO GLASS BEADS

Tubing containing glass beads was treated as above with and without the protein and the adhesion of platelets determined as described above. The results are shown in Table 9 below which shows that the protein was able to significantly reduce platelet adhesion to glass beads (15–20% at the dose tried—see Example 4).

TABLE 9

| Expt No. | Pre-incubation time (minutes) | Reduction in platelet no. (%). | | |
|---|---|---|---|---|
| | | Control | +Protein | Boiled Protein |
| 1 | 0–2 | 74 | 59 | — |
| 2 | 0–2 | 98 | 79 | 86 |

Whole blood was pumped over a glass bead column (Adeplat) which had been pre-treated with or without the protein (5000 units/ml) or with boiled (1–2 min) protein. Platelet numbers which passed through the column were counted in a Coulter counter as above.

I claim:

1. A purified protein isolated from the leech species *Hirudo medicinalis,* said purified protein being substantially free of leech-derived collagenase, capable of binding to native collagen in such a way that substantially no cleavage breakdown products of collagen molecules occur on SDS-PAGE, capable of inhibiting collagen-induced platelet aggregation or adhesion, having a molecular weight in the range of 60–70 kilodaltons in a reduced form and exhibiting optimum activity in inhibiting collagen-induced platelet aggregation at a pH of about 8.0 in the presence of co-factors $Ca^{+2}$ and $Mg^{+2}$, said protein being obtained from secretions or extract of the tissue of said leech species by performing chromatographic purification steps using buffers containing about 12% ethanol to prevent protein loss by adsorption and removing said ethanol to obtain said purified protein.

2. A method of preventing platelet aggregation or adhesions on thrombogenic matrices used in vitro, comprising coating said thrombogenic matrices with the protein of claim 1.

3. A pharmaceutical or veterinary formulation comprising a protein according to claim 1 and a pharmaceutically acceptable carrier.

4. A formulation of claim 3 further comprising a thrombolytic agent.

5. A formulation of claim 4 wherein said thrombolytic agent is selected from the group consisting of a plasminogen activator and hementin.

6. A formulation of claim 3 further comprising an anti-coagulant.

7. A formulation of claim 6 wherein said anti-coagulant is selected from the group consisting of hirudin and heparin.

8. A formulation of claim 3 for treatment of pathological conditions involving platelet aggregation or adhesion.

9. A formulation of claim 3 for preventing platelet aggregation or adhesion.

10. A formulation of claim 3 for use in maintaining prolonged bleeding following plastic surgery or microsurgery.

11. An implantable or extracorporeal device for use in contact with body fluids, said device having a protein according to claim 1 immobilized thereon wherein said protein renders the device surface substantially biocompatible and thromboresistant.

12. A coating for medical devices comprising the formulation of claim 3.

13. A coating of claim 12 wherein said medical devices are selected from the group consisting of indwelling catheters, vascular shafts, artificial organs and sutures.

* * * * *